(12) United States Patent
Mehta

(10) Patent No.: US 8,008,532 B2
(45) Date of Patent: Aug. 30, 2011

(54) PROCESSES AND METHODS FOR EXTRACTION AND PURIFICATION OF LUTEIN FROM MARIGOLD ESTERS

(75) Inventor: Sevanti Mehta, Houston, TX (US)

(73) Assignee: Unibar Corporation, Houston, TX (US)

( * ) Notice: Subject to any disclaimer, the term of this patent is extended or adjusted under 35 U.S.C. 154(b) by 45 days.

(21) Appl. No.: 12/560,245

(22) Filed: Sep. 15, 2009

(65) Prior Publication Data

US 2011/0065965 A1    Mar. 17, 2011

(51) Int. Cl.
  *C07C 35/21*    (2006.01)
  *A61K 36/28*    (2006.01)
(52) U.S. Cl. ........................................ 568/816; 424/764
(58) Field of Classification Search .......................... None
  See application file for complete search history.

(56) References Cited

U.S. PATENT DOCUMENTS

| 5,648,564 A * | 7/1997 | Ausich et al. ................. 568/834 |
| 6,262,284 B1 * | 7/2001 | Khachik .......................... 554/14 |
| 6,380,442 B1 * | 4/2002 | Madhavi et al. .............. 568/816 |
| 2005/0139145 A1 * | 6/2005 | Quesnel ............................ 117/2 |

* cited by examiner

*Primary Examiner* — Brian J Davis
(74) *Attorney, Agent, or Firm* — Steve P. Hassid; Silicon Edge Law Group LLP

(57) ABSTRACT

A process is disclosed for simultaneously extracting, saponifying, and isolating lutein without the use of harmful organic solvents. In one embodiment the method includes (a) dispersing Marigold oleoresin in an alkane hydrocarbon alkanol solution, (b) adding a potassium hydroxide to the Marigold oleoresin and alkane hydrocarbon alkanol solution to form a homogenous solution of Marigold oleoresin, (c) refluxing the homogeneous solution until ester hydrolysis of the Marigold oleoresin is completed, (d) cooling the homogeneous solution and allowing it to settle until lutein crystals are formed, and (e) washing the lutein crystals with methanol-hexane solution to separate and filter them from the solvents.

18 Claims, 2 Drawing Sheets

| BATCH NO | Charged Qty (MOR) KG | Product Obtained (Lutein) Kg | YIELD (%) | XANTHOPHYLLS (G/KG) | PURITY (%) | TRANSLUTEIN (HPLC) % | RESIDUAL HEXANE (PPM) | RESIDUAL METHANOL (PPM) | MOISTURE (%) |
|---|---|---|---|---|---|---|---|---|---|
| 6008/2 | 380.000 | 24.500 | 6.44 | 810 | 75.5 | 93.6 | 45 | 3 | 1 |
| 6008/3 | 760.000 | 64.500 | 8.48 | 890 | 83.2 | 93.5 | 26 | 27 | 1 |
| 6008/4 | 760.000 | 73.000 | 9.6 | 885 | 82.5 | 93.22 | 2 | 2 | 2 |
| 6008/5 | 380.000 | 28.500 | 7.5 | 830 | 78.0 | 94.0 | 7 | 6 | 1 |
|  | 2280.000 | 190.500 | 8.36 |  |  |  |  |  |  |

FIG. 2

PROCESSES AND METHODS FOR EXTRACTION AND PURIFICATION OF LUTEIN FROM MARIGOLD ESTERS

BACKGROUND

1. Field of the Invention

The present disclosure is generally related to methods for manufacturing and isolating lutein. More specifically, the present disclosure is directed to processes for extraction, isolation, and purification of lutein crystals from Marigold esters of a plant. Additionally, the present disclosure is directed to the alkaline hydrolysis of Marigold oleoresin in a homogeneous medium followed by isolating the required solid material via washing off adhering by-products and other contaminants using the same solvents that are used during the hydrolysis stage to provide lutein crystals from a plant source that are free from harmful or otherwise undesirable organic solvents.

2. Background

Lutein is basically an alcohol component of Marigold esters. Separation of organic acids from their esters with different types of alcohols and isolation of the alcohol components in the unsaponifiable matter have been practiced by chemists for several decades now and numerous methods are known in the art. What is not known in the art is an optimized method of manufacturing and isolating lutein that results in quality lutein with acceptable yields and without the use of harmful solvents or solvent residues.

There are several major disadvantages to known methods of manufacturing and isolating lutein. Furthermore, many of the organic solvents used in known processes are harmful, not desirable, add expense to the procedure and lower the resulting yield of lutein. The present disclosure overcomes these problems and provides various benefits and advantages.

BRIEF SUMMARY OF THE INVENTION

This disclosure includes methods for simultaneous extraction and hydrolysis (saponification) procedures for isolation and purification of lutein from Marigold flowers and related plant products/compounds.

In one embodiment of the present disclosure, a method is disclosed for the extraction, saponification, and isolation of lutein crystals from a plant source without the use of harmful organic solvents. The method comprises a) dispersing Marigold oleoresin in an alkane hydrocarbon alkanol solution, b) adding a potassium hydroxide to the Marigold oleoresin and alkane hydrocarbon alkanol solution to form a homogenous solution of Marigold oleoresin, c) refluxing the homogeneous solution until ester hydrolysis of the Marigold oleoresin is completed, d) cooling the homogeneous solution and allowing it to settle until lutein crystals are formed, and e) washing the lutein crystals with methanol-hexane solution to separate and filter them from the solvents.

In another embodiment of the present disclosure, a method is provided for the extraction and hydrolysis of lutein esters from Marigold petals without the use of harmful solvents. The method comprises extracting and saponifying lutein esters from Marigold petals by contacting said petals with a solution comprising hexane, methanol and then a solution of potassium hydroxide to obtain a mixture comprising lutein, removing unwanted materials from the mixture, washing the mass with methanol-hexane and collecting lutein crystals.

In another embodiment of the present disclosure, a method is provided for the extraction, saponification and isolation of lutein crystals. The method comprises a) contacting Marigold oleoresin with a methanol solution of hexane to create a first solution, b) contacting the first solution with potassium hydroxide to form a second solution, c) refluxing the second solution until ester hydrolysis of the Marigold oleoresin of the second solution is completed, d) allowing the second solution to cool and settle until lutein crystals are formed and e) washing the lutein crystals with a methanol-hexane aqueous solution.

In yet another embodiment of the present disclosure, a method is provided for the extraction, saponification, and isolation of lutein crystals. The method comprises a) providing approximately one part Marigold oleoresin and processing through desolventizer (refluxing unit), b) adding approximately 2.5 parts hexane and 2.5 parts methanol to the Marigold oleoresin, c) dissolving approximately 0.15 parts KOH in less than 0.15 parts methanol, d) filtering the KOH methanol mixture and adding into the desolventizer (refluxing unit), e) applying steam of approximately 65 degrees to 75 degrees Celsius, and (f) stirring until the ester hydrolysis is substantially complete and cooling for at least three hours.

In yet another embodiment of the present disclosure, a method is provided for the extraction, saponification and isolation of lutein crystals. The method comprises a) providing approximately 100 kg Marigold oleoresin and processing through desolventizer (Refluxing unit), b) adding approximately 250 kg hexane and 250 kg methanol to the Marigold oleoresin, c) dissolving approximately 15 kg KOH in a minimal amount of methanol, d) filtering the KOH methanol mixture and adding into the desolventizer (Refluxing unit), e) applying steam of approximately 65 degrees to 75 degrees Celsius to the mixture and stirring for three to four hours, f) filtering miscella through a filter (e.g., round filter), g) transferring clear portion of liquid to evaporator resulting in residue remaining on filter, g) washing residue with methanol and hexane to remove any alkali and wax, h) placing residue in desolventizer and removing the solvent residue less than approximately 50 ppm (total) and, if the residue contains moisture, drying it in a dryer (e.g., vacuum dryer).

In yet another embodiment of the present disclosure, a method is provided for the extraction, saponification, and isolation of lutein crystals. The method comprises a) adding approximately one part Marigold oleoresin and approximately 2.5 parts hexane and 2.5 parts methanol to a desolventizer or refluxing unit to create a Marigold oleoresin mixture, b) dissolving approximately 0.15 parts KOH in enough methanol that the KOH fully dissolves in the methanol, c) filtering the KOH methanol mixture and adding into the desolventizer or refluxing unit to create a second Marigold oleoresin mixture, d) applying steam and stirring the second Marigold oleoresin mixture until the ester hydrolysis is substantially complete, e) cooling or allowing the second Marigold oleoresin mixture to cool, f) filtering the miscella of the second Marigold oleoresin mixture through a filter, g) transferring the clear portion of liquid of the second Marigold oleoresin mixture to evaporator and leaving the residue of the second Marigold oleoresin mixture remaining on filter, h) washing the residue of the second Marigold oleoresin mixture with methanol and hexane, and i) adding the residue of the second Marigold oleoresin mixture in desolventizer to remove any solvent residue.

In one aspect of at least one embodiment of the present disclosure, the extraction and saponification are conducted simultaneously.

In another aspect of at least one embodiment of the present disclosure, the alkane hydrocarbon is hexane.

In yet another aspect of at least one embodiment of the present disclosure, the potassium hydroxide is methanolic potassium hydroxide.

In yet another aspect of at least one embodiment of the present disclosure, the method further includes drying the lutein crystals.

In yet another aspect of at least one embodiment of the present disclosure, the method further includes packing the dried lutein crystals.

In yet another aspect of at least one embodiment of the present disclosure, the method includes purifying the lutein crystals by dissolving the crystals to create a solution and passing the solution of lutein through a column packed with n-silica gel and isolating pure lutein.

In yet another aspect of at least one embodiment of the present disclosure, the dried lutein crystals are free from harmful or otherwise undesirable organic solvents.

Other methods and systems are also disclosed.

DRAWINGS

The above-mentioned features and objects of the present disclosure will become more apparent with reference to the following description taken in conjunction with the accompanying drawings in which:

FIG. 2 is a table demonstrating the results of experiments using the methods of the present disclosure and identifying various attributes, including but not limited to the amount, purity and yield of lutein obtained using methods and procedures of the present disclosure.

DETAILED DESCRIPTION OF THE INVENTION

Figure 1:
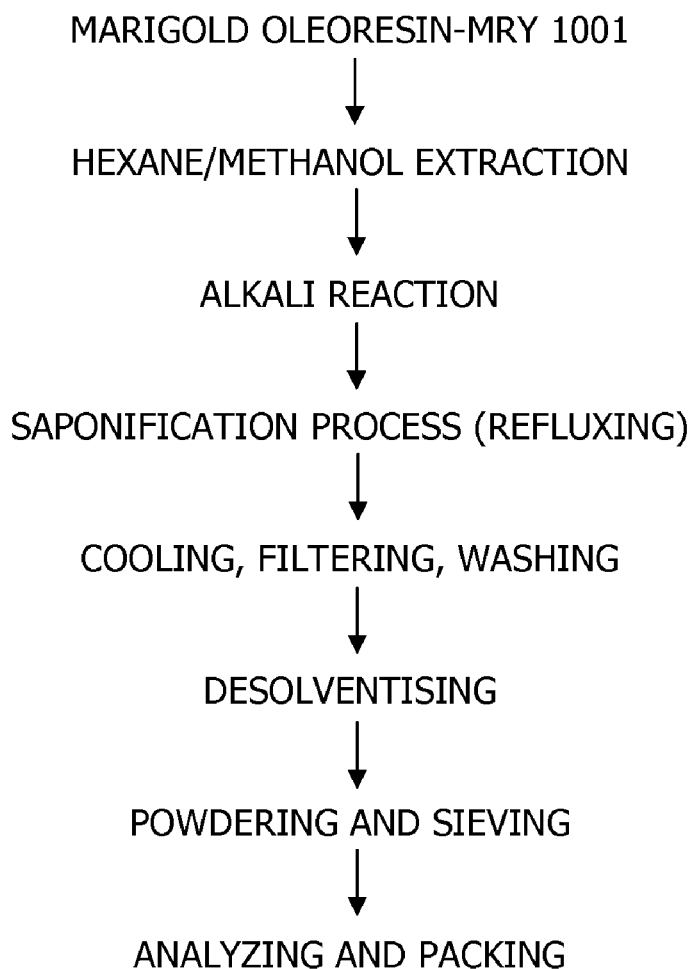
FIG. 1 is a flow chart demonstrating the various steps associated with at least one embodiment of the present disclosure.

The present disclosure includes methods for simultaneous extraction and hydrolysis (saponification) procedures for isolation and purification of lutein from Marigold flowers and related plant products/compounds.

In one embodiment of the present disclosure, a method is disclosed for the extraction, saponification and isolation of lutein crystals from a plant source without the use of harmful organic solvents. The method comprises a) dispersing Marigold oleoresin in an alkane hydrocarbon alkanol solution, b) adding a potassium hydroxide to the Marigold oleoresin and alkane hydrocarbon alkanol solution to form a homogenous solution of Marigold oleoresin, c) refluxing the homogeneous solution until ester hydrolysis of the Marigold oleoresin is completed, d) cooling the homogeneous solution and allowing it to settle until lutein crystals are formed; and e) washing the lutein crystals with methanol-hexane solution to separate and filter them from the solvents.

In another embodiment of the present disclosure, a method is provided for the extraction and hydrolysis of lutein esters from Marigold petals without the use of harmful solvents. The method comprises extracting and saponifying lutein esters from Marigold petals by contacting said petals with a solution comprising hexane, methanol and then a solution of potassium hydroxide to obtain a mixture comprising lutein, removing unwanted materials from the mixture, washing the mass with methanol-hexane and collecting lutein crystals.

In another embodiment of the present disclosure, a method is provided for the extraction, saponification and isolation of lutein crystals. The method comprises a) contacting Marigold oleoresin with a methanol solution of hexane to create a first solution, b) contacting the first solution with potassium hydroxide to form a second solution, c) refluxing the second solution until ester hydrolysis of the Marigold oleoresin of the second solution is completed, d) allowing the second solution to cool and settle until lutein crystals are formed and e) washing the lutein crystals with a methanol-hexane aqueous solution.

In yet another embodiment of the present disclosure, a method is provided for the extraction, saponification, and isolation of lutein crystals. The method comprises a) providing approximately one part Marigold oleoresin to remove any solvents through a desolventizer and/or refluxing unit, b) adding approximately 2.5 parts hexane and 2.5 parts methanol to the Marigold oleoresin, c) dissolving approximately 0.15 parts KOH in less than 0.15 parts methanol, d) filtering the KOH methanol mixture and adding into the desolventizer (refluxing unit), e) applying steam of approximately 65 degrees to 75 degrees Celsius, and (f) stifling until the ester hydrolysis is substantially complete and cooling for at least three hours.

In yet another embodiment of the present disclosure, a method is provided for the extraction, saponification and isolation of lutein crystals. The method comprises a) providing approximately 100 kg Marigold oleoresin and processing through desolventizer (Refluxing unit), b) adding approximately 250 kg hexane and 250 kg methanol to the Marigold oleoresin, c) dissolving approximately 15 kg KOH in a minimal amount of methanol, d) filtering the KOH methanol mixture and adding into the desolventizer (Refluxing unit), e) applying steam of approximately 65 degrees to 75 degrees Celsius to the mixture and stirring for three to four hours, f) filtering miscella through a filter (e.g., round filter), g) transferring clear portion of liquid to evaporator resulting in residue remaining on filter, g) washing residue with methanol and hexane to move any alkali and wax, h) placing residue in desolventizer and removing the solvent residue less than approximately 50 ppm (total) and, if the residue contains moisture, drying it in a dryer (e.g., vacuum dryer).

In yet another embodiment of the present disclosure, a method is provided for the extraction, saponification, and isolation of lutein crystals. The method comprises a) adding approximately one part Marigold oleoresin and approximately 2.5 parts hexane and 2.5 parts methanol to a desolventizer or refluxing unit to create a Marigold oleoresin mixture, b) dissolving approximately 0.15 parts KOH in enough methanol that the KOH fully dissolves in the methanol, c) filtering the KOH methanol mixture and adding into the desolventizer or refluxing unit to create a second Marigold oleoresin mixture, d) applying steam and stirring the second Marigold oleoresin mixture until the ester hydrolysis is substantially complete, e) cooling or allowing the second Marigold oleoresin mixture to cool, f) filtering the miscella of the second Marigold oleoresin mixture through a filter, g) transferring the clear portion of liquid of the second Marigold oleoresin mixture to evaporator and leaving the residue of the second Marigold oleoresin mixture remaining on filter, h) washing the residue of the second Marigold oleoresin mixture with methanol and hexane, and i) adding the residue of the second Marigold oleoresin mixture in desolventizer to remove any solvent residue.

In one aspect of at least one embodiment of the present disclosure, the extraction and saponification are conducted simultaneously.

In another aspect of at least one embodiment of the present disclosure, the alkane hydrocarbon is hexane.

In yet another aspect of at least one embodiment of the present disclosure, the potassium hydroxide is methanolic potassium hydroxide.

In yet another aspect of at least one embodiment of the present disclosure, the method further includes drying the lutein crystals.

In yet another aspect of at least one embodiment of the present disclosure, the method further includes packing the dried lutein crystals.

In yet another aspect of at least one embodiment of the present disclosure, the method includes purifying the lutein crystals by dissolving the crystals to create a solution and passing the solution of lutein through a column packed with n-silica gel and isolating pure lutein.

In yet another aspect of at least one embodiment of the present disclosure, the dried lutein crystals are free from harmful or otherwise undesirable organic solvents.

One skilled in the relevant art may recognize, however, that the methods and techniques described herein may be practiced without one or more of the specific details, or with other methods, resources, materials, etc. In other instances, well-known structures, resources, or operations have not been shown or described in detail merely to avoid obscuring aspects of various exemplary techniques or because they are well known in the art.

While various examples and methods have been illustrated and described, it is to be understood that the methods and techniques are not limited to the precise configuration, order of steps and resources described above. Various modifications, changes, and variations apparent to those skilled in the art may be made in the arrangement, operation, and details of the methods and techniques disclosed herein without departing from their practical scope.

While the methods have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar methods. The present disclosure includes any and all embodiments of the following claims.

The invention claimed is:

1. A method for the saponification and isolation of lutein crystals, the method comprising:
   a) dispersing Marigold oleoresin in an alkane hydrocarbon alkanol solution;
   b) adding potassium hydroxide to the Marigold oleoresin and alkane hydrocarbon alkanol solution, to form a homogenous solution of Marigold oleoresin;
   c) refluxing the homogeneous solution until ester hydrolysis of the Marigold oleoresin is completed;
   d) cooling the homogeneous solution and allowing it to settle until lutein crystals are formed; and
   e) washing the lutein crystals with methanol-hexane aqueous solution to separate and filter them from the solvents.

2. The method of claim 1, wherein the alkane hydrocarbon is hexane.

3. The method of claim 2, wherein the potassium hydroxide is methanolic potassium hydroxide.

4. The method of claim 2, additionally comprising drying the lutein crystals.

5. The method of claim 4, additionally comprising packing the dried lutein crystals.

6. A method for the extraction and hydrolysis of lutein esters, the method comprising: extracting and saponifying lutein esters from Marigold petals by contacting said petals with a solution comprising hexane, methanol and then a solution of potassium hydroxide to obtain a mixture comprising lutein, removing unwanted materials from the mixture, washing the mass with methanol-hexane and collecting lutein crystals.

7. The method of claim 1, wherein extraction and hydrolysis are conducted simultaneously.

8. The method of claim 6, wherein the potassium hydroxide is methanolic potassium hydroxide.

9. The method of claim 8, additionally comprising drying the lutein crystals.

10. The method of claim 9, additionally comprising packing the dried lutein crystals.

11. The method of claim 6, wherein the Marigold petals, prior to extraction, are milled to a meal.

12. The method of claim 6, further comprising purifying crystals by dissolving the crystals to create a solution and passing the solution of lutein through a column packed with n-silica gel and isolating pure lutein.

13. A method for the saponification and isolation of lutein crystals, the method comprising:
   a) contacting Marigold oleoresin with a solution of hexane to create a first solution;
   b) contacting the first solution with potassium hydroxide to form a second solution;
   c) refluxing the second solution until ester hydrolysis of the Marigold oleoresin of the second solution is completed;
   d) allowing the second solution to cool and settle until lutein crystals are formed; and
   e) washing the lutein crystals with a methanol-hexane aqueous solution.

14. The method of claim 13, wherein the potassium hydroxide is methanolic potassium hydroxide.

15. The method of claim 13, additionally comprising drying the lutein crystals.

16. The method of claim 15, additionally comprising packing the dried lutein crystals.

17. The method of claim 14, wherein lutein crystals are free from organic solvents.

18. A method of for the saponification, and isolation of lutein crystals, the method comprising:
   a) adding approximately one part Marigold oleoresin and approximately 2.5 parts hexane and 2.5 parts methanol to a desolventizer or refluxing unit to create a Marigold oleoresin mixture;
   b) dissolving approximately 0.15 parts KOH in enough methanol that the KOH fully dissolves in the methanol;
   c) filtering the KOH methanol mixture and adding into the desolventizer or refluxing unit to create a second Marigold oleoresin mixture;
   d) applying steam and stirring the second Marigold oleoresin mixture until refluxing process is substantially complete;
   e) cooling or allowing the second Marigold oleoresin mixture to cool;
   f) filtering the miscella of the second Marigold oleoresin mixture through a filter;
   g) transferring the clear portion of liquid of the second Marigold oleoresin mixture to an evaporator and leaving the residue of the second Marigold oleoresin mixture remaining on filter;
   h) washing the residue of the second Marigold oleoresin mixture with methanol and hexane; and
   i) adding the residue of the second Marigold oleoresin mixture in desolventizer to remove any solvent residue.

* * * * *